United States Patent [19]

Long

[11] Patent Number: 5,562,658

[45] Date of Patent: Oct. 8, 1996

[54] LASER-POWERED SURGICAL DEVICE FOR MAKING INCISIONS OF SELECTED DEPTH

[75] Inventor: Gary Long, Cincinnati, Ohio

[73] Assignee: SNJ Company, Inc., Cincinnati, Ohio

[21] Appl. No.: 217,910

[22] Filed: Mar. 25, 1994

[51] Int. Cl.⁶ .................................................. A61B 17/36
[52] U.S. Cl. ............................................................. 606/15
[58] Field of Search ........................... 606/172, 167, 606/15, 16, 27, 28, 29, 32, 39, 45; 604/22

[56] References Cited

U.S. PATENT DOCUMENTS

| | | | |
|---|---|---|---|
| 4,994,060 | 2/1991 | Rink et al. ........................... | 606/15 |
| 5,164,945 | 11/1992 | Long et al. . | |
| 5,300,066 | 4/1994 | Manoukian et al. ................ | 606/15 |
| 5,306,274 | 4/1994 | Long . | |
| 5,342,358 | 8/1994 | Daikuzono .......................... | 606/15 |
| 5,344,420 | 9/1994 | Hilal et al. ......................... | 606/28 |
| 5,352,221 | 10/1994 | Fumich ............................... | 606/15 |

*Primary Examiner*—Angela D. Sykes
*Assistant Examiner*—Sonya Harris-Ogugua
*Attorney, Agent, or Firm*—Lowe, Price, LeBlanc & Becker

[57] ABSTRACT

A laser-powered surgical tool comprises an elongate distal end portion suitable for laparoscopic surgery, and contains an extreme distal end portion by which a laser-powered tip is applied to tissue to generate incisions of predetermined but adjustable depth therein. The tissue being incised is held by suction in an optimum position for advancing the incision while, simultaneously, any gases and incidental fluids generated or released by the advancing incision are removed by suction applied immediately around the incision point as the incision proceeds.

24 Claims, 6 Drawing Sheets

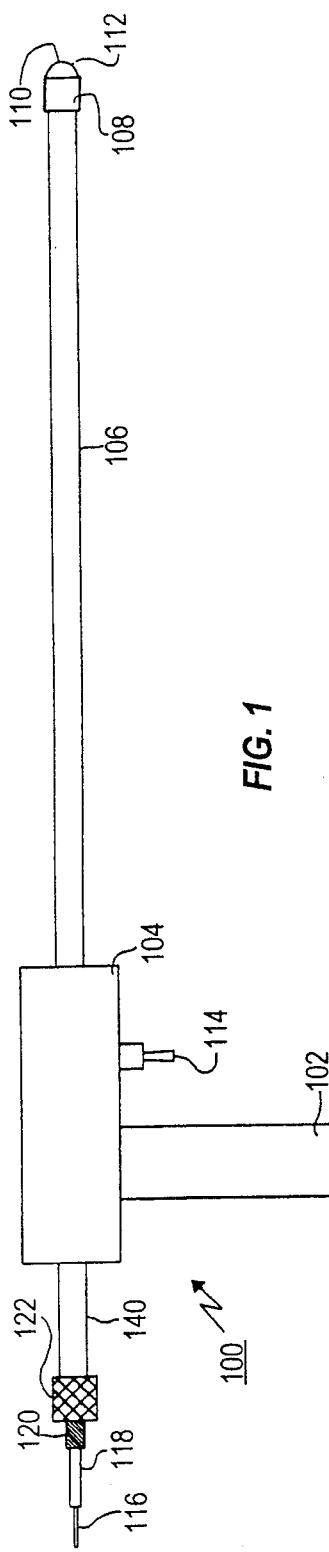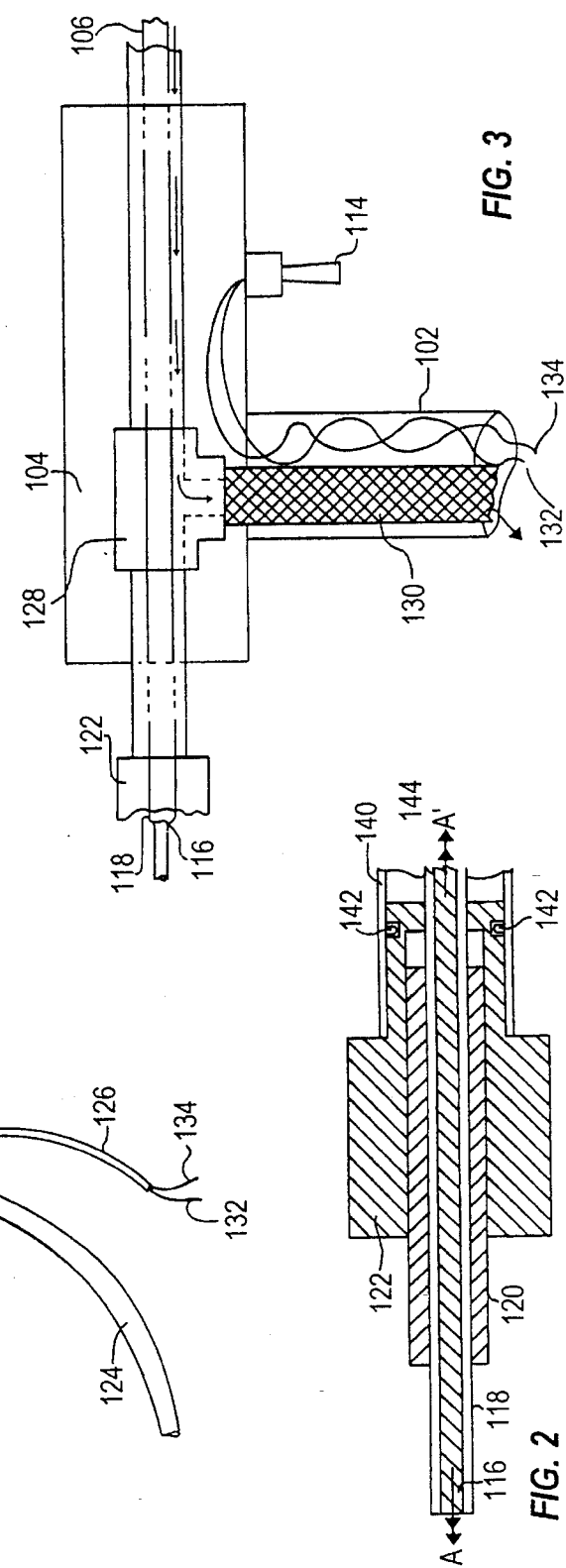
FIG. 1
FIG. 2
FIG. 3

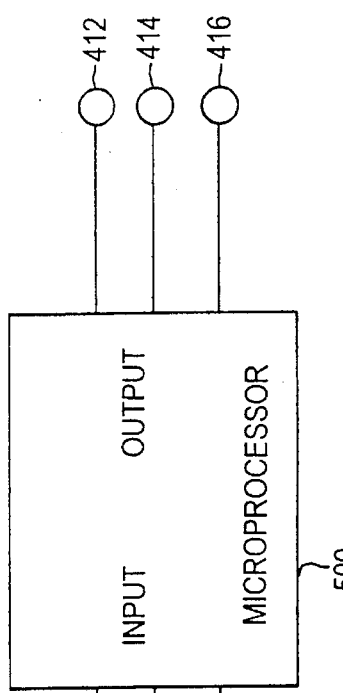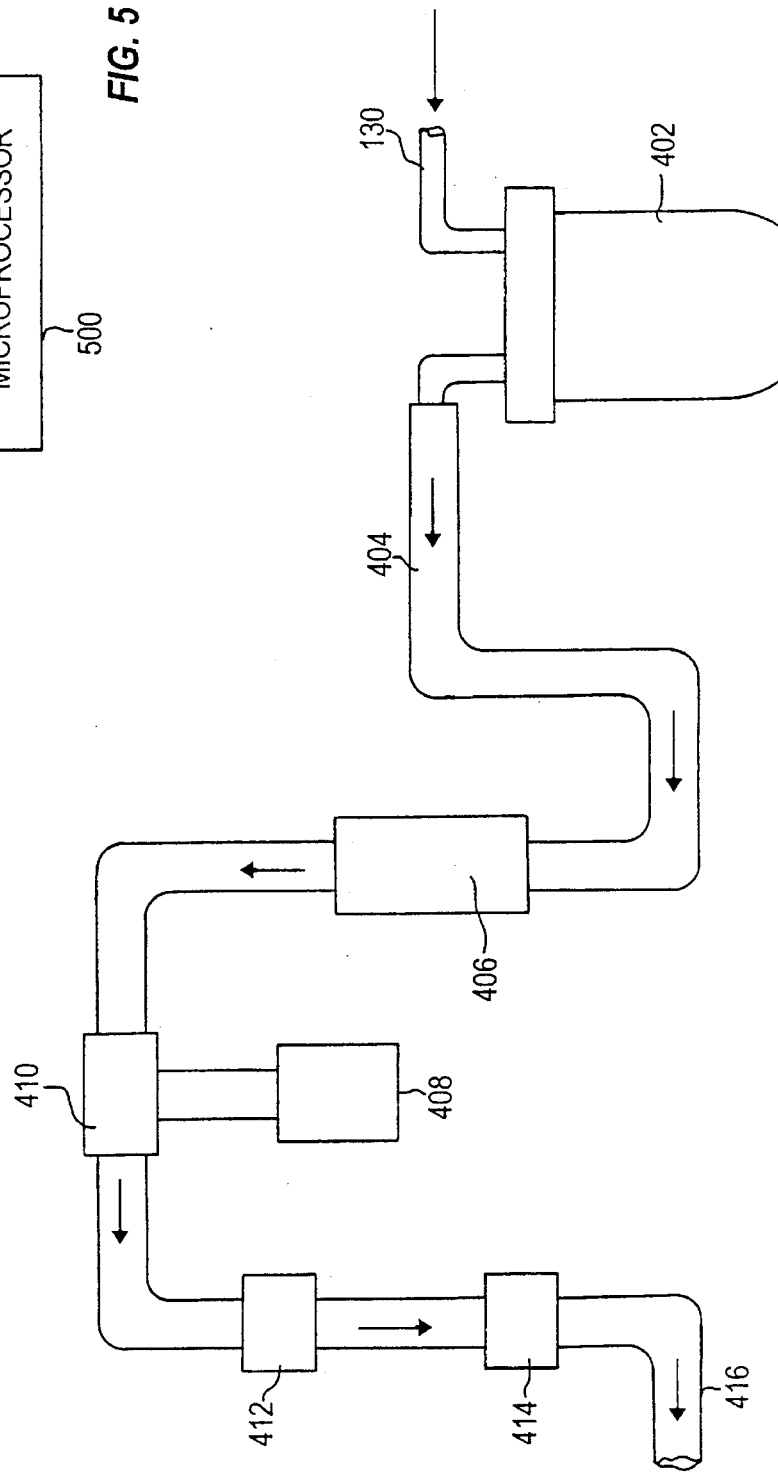

LASER-POWERED SURGICAL DEVICE FOR MAKING INCISIONS OF SELECTED DEPTH

FIELD OF THE INVENTION

This application relates to laser-powered surgical tools for making incisions in tissue, and more particularly to laser-powered tools suitable for laparoscopic surgery to make incisions of adjustably controlled depth in soft tissue.

BACKGROUND OF THE PRIOR ART

Recent successes in surgical procedures such as laparoscopic cholecystectomy have led to the adaptation of other routine surgical procedures to a laparoscopic approach. Thus, for example, procedures such as hernia repair, appendectomy, and most recently, vagotomy, etc., have been successfully performed under laparoscopic guidance.

It is estimated that about twenty million people in the United States suffer from peptic ulcer disease. The overwhelming majority of these patients are adequately managed with conventional medical treatment. Nonetheless, 5–10% of patients with peptic ulcer disease very likely will suffer from failed medical treatment or related complications such as bleeding and perforations. For this group of patients a vagotomy with or without gastric section has proved to be a safe and effective form of treatment.

Many patients, however, are reluctant to undergo major abdominal surgery, at least in part due to the typical subsequent prolonged hospitalization, recovery periods, post-operative discomfort, and cosmetic considerations.

It is considered that laparoscopic highly selective vagotomy may offer many sufferers a safe, feasible and effective alternative to conventional ulcer surgery. It offers many of the advantages associated with a traditional highly selective vagotomy and avoids many of the known disadvantages of a laparotomy. The procedure provides a treatment of peptic ulcer disease, with a relatively short hospital stay, involves minimal post-operative discomfort and allows the patient an early return to work. It is therefore a viable alternative to lifelong medical therapy or an open abdominal operation.

The current indications of laparoscopic vagotomy are limited to the treatment of intractable disease and acute perforation. Operations for both of these conditions have been successfully completed in the United States and Europe. With further experience and refinement of surgical technique, perhaps other conditions such as perforation, bleeding and obstruction may also indicate a role for laparoscopic vagotomy.

The pre-operative evaluation for laparoscopic vagotomy is very similar to that for conventional ulcer surgery. Before surgery, the patient undergoes gastro-intestinal endoscopy as well as contrast studies to determine the extent and severity of the disease. In addition, to evaluate the effectiveness of this new procedure all patients ideally should undergo pre- and post-operative gastric acid studies.

Due to the disadvantages of a bilateral truncal vagotomy and because a conventional highly selective vagotomy may be very difficult to perform under laparoscopic guidance, several modifications of standard ulcer operations are needed. At the University of Maryland, doctors have developed a modified, highly selective vagotomy which can be performed under laparoscopic guidance. One successful technique consists of a posterior truncal vagotomy combined with an anterior highly selective vagotomy performed in a standard fashion by individual ligation of the neurovascular bundles along the lesser curve of the stomach. The procedure is performed under general anesthesia.

The operation is begun with a 1.5 centimeter incision made at the umbilicus. The subcutaneous tissue is gently separated down to the level of the facia. A Veress insufflation needle is introduced into the abdominal cavity. Confirmation of appropriate positioning of the needle is made using standard techniques and carbon dioxide is instilled via an automatic insufflator until a pressure of 12 mm. of mercury is achieved. Accumulation of a appropriate level of pneumoperitoneum is confirmed by monitoring of the intra-abdominal pressure.

The laparoscope with the attached video camera is then inserted into the abdominal cavity. A thorough diagnostic laparoscopy is performed with inspection of the liver, gallbladder, small and large intestine, pelvic structures, and finally, the stomach. The stomach may be moderately distended following the induction of anesthesia. It is considered important to achieve adequate decompression of the stomach prior to beginning the operative dissection.

Accessory trocars may be inserted into the abdominal cavity under direct laparoscopic guidance to minimize the risk of injury to the abdominal viscera. Ports to receive trocars may also be placed either in the left mid-abdomen or just below the xiphoid process on the left.

The operation continues with insertion of a liver retractor which is opened and placed under the left lobe of the liver. This retraction provides excellent exposure of the gastro-esophageal junction, a critical maneuver in the performance of a laparoscopic vagotomy. The retractor, once properly positioned, is secured in place.

The region of the gastro-esophageal junction is then closely inspected.

The esophagus and diaphragmatic crus is mobilized to expose the posterior vagus trunk. The posterior vagal trunk can be ligated with surgical clips, after which a segment of nerve can be excised and sent for further histologic confirmation. Occasionally, a small accessory vagal branch may be identified along the lateral aspect of the esophagus. It is dissected free, ligated and divided.

The next step is to identify the anterior vagus nerve at the gastro-esophageal junction. The course of the anterior nerve along the lesser curve of the stomach is visualized. Each neurovascular bundle is identified and carefully dissected free from the underlying gastric wall, ligated with surgical clips and then transected. Following completion of the anterior highly selective vagotomy, the operative field is irrigated with normal saline. The previously placed clips are inspected to ensure adequate hemostasis.

Following completion of the laparoscopic vagotomy, the laparoscope and surgical trocars are removed from the abdominal cavity. The facial incisions are all closed with a single interrupted absorbable sutures. The skin is reapproximated with surgical clips and sterile dressings are applied.

An alternative to a posterior truncal vagotomy and an anterior highly selective vagotomy is the performance of a bilateral truncal vagotomy. This may be performed either as a planned procedure or following inadvertent injury to the anterior trunk during operative dissection. In such cases, it is necessary to perform drainage of the stomach. Such drainage may be accomplished by either direct pyoplasty, endoscopic balloon dilation or a pyloromyotomy.

Initial results with these relatively new procedures have been encouraging. It appears that a modified laparoscopic highly selective vagotomy may offer a viable alternative to conventional ulcer surgery. Certainly, an operative procedure associated with a one to two-day hospitalization period and a low operative morbidity, may become a valuable alternative to lifelong medical treatment or the risks of a major abdominal operation.

As surgeons and others skilled in the relevant art will readily appreciate, the above-described known surgical procedures are complex, and even when done very carefully will involve the risk of perforation, bleeding, infection and the like if the incisions are made too deep. It is therefore clearly desirable to develop alternative apparatus and methods for performing laparoscopic vagotomy with very precise incisions to predetermined depth into tissues. Additionally, it is highly desirable to perform the incisions in such a manner that any bodily fluids that do leak from the incision are immediately coagulated, e.g., by applying heat. However, the application of a high enough temperature to effect division and separation of tissue and/or coagulation as described is likely to generate vapors and gases. These can obscure viewing of the operational site by the laparoscopic camera. Therefore, continuous suction of these fluids (liquids or gases and vapors) from the operative field is also highly desirable. The suction must, however, be very precisely applied and controlled to maintain the needed constant insufflation of the abdominal cavity.

All of these needs are very simply and effectively addressed by the present invention, as described below.

SUMMARY OF THE INVENTION

It is a principal object of this invention to provide a surgical tool which enables a surgeon/user to determine a priori the depth of cut in making an incision in tissue during surgery.

Another object of this invention is to provide a laser-powered surgical tool formed for convenient use in laparoscopic surgery to make incisions of controlled depth into soft tissue with immediate removal of smoke, gases, and incidental fluids generated or released at a point of incision.

Yet another object of this invention is to provide an improved laparoscopic surgical tool with a distal end structure which, by itself, firmly holds contacted tissue as the tool is operatively moved over the tissue to generate incisions of controlled depth.

An even further object of this invention is to provide, for an improved laser-powered elongate surgical tool, an operative end structure which provides suction immediately around a point of incision to remove gaseous effluents generated during surgery while precisely holding the tissue as the incision progresses.

In another aspect of this invention, there is provided a method for performing laser-powered surgical incisions of predetermined but readily adjustable depth into soft tissue during a surgical operation.

Another related object of this invention is to provide a method by which laser-powered incisions are controlled to be of a predetermined depth, while simultaneously holding the tissue being incised to a laser-powered incision tip and removing from the incision site fluids produced or released during surgery.

Yet another related object of this invention is to provide a method for performing laparoscopic surgery by forming incisions of predetermined depth while maintaining a clear field of view by simultaneously removing from an incision site any gases generated during laser surgery, holding the tissue to be incised in position for ongoing incision, and reducing incidental bleeding by coagulating body fluids at and along surgical incisions.

These and other related objects are realized in a first aspect of this invention by providing an improved tool for making precise surgical incisions of predetermined depth into a soft tissue by application of a tissue-severing distal tip. The improvement comprises providing in the surgical tool means for presenting a smoothly rounded surface for contacting the tissue which is to be incised, the rounded surface being formed to surround the tip with an annular opening defined between an outer surface of the tip and the surrounding rounded surface. With this tool, when soft tissue being incised is pressed by the rounded surface and is thus locally stretched around the tip element within the annular opening surrounding the tip element, only a predetermined length of a tissue-severing portion of the tip is permitted to penetrate the stretched soft tissue. Movement of the surgical tool along the tissue then effects the desired incision to the selected predetermined depth.

In another aspect of the invention, at least the tissue-severing portion of the tip is heated by transmitting laser energy to the tip for absorption and conversation thereof into thermal energy at a surface region in the tissue-severing portion. Application of this heated tip generates thermal disruption of the tissue and effects the desired incision to the selected predetermined depth, with the added benefit that the high temperature coagulates at least some of the fluids, e.g., blood and/or plasma, released in the course of making the incision.

In yet another aspect of this invention, suction is provided to the annular space immediately surrounding the tissue-severing portion of the tip, so that uncoagulated liquids, gases and vapors released by contact between the heated tip and the tissue are sucked away from the immediate vicinity of the incision site as the incision proceeds.

In yet another aspect of this invention there is provided a method for making incisions of predetermined depth into soft tissue, comprising the steps of providing at an operative distal end of a surgical tool a tissue-contact surface with an opening and, within the opening, providing a tissue-severing tip which projects outwardly from the third tissue-contact surface by a predetermined length, and applying the third surface to the soft tissue to cause the soft tissue to stretch across the opening with the tissue-severing tip penetrating into the stretched soft tissue only to a predetermined penetration depth, and moving the applied surgical tool so that the tissue-severing tip makes an incision of an incision depth which is no greater than the penetration depth.

In a related further aspect of this invention, suction is provided to the opening to suck away from the incision site any fluids released during making of the incision, and heating the tissue-severing tip so that soft tissue contacting the same is thermally disrupted to enable formation of the incision with at least some of the released fluids being thermally coagulated.

BRIEF DESCRIPTION OF THE DRAWING

FIG. 1 is a schematic side elevation view of a handheld surgical tool according to a preferred embodiment of this invention.

FIG. 2 is an enlarged view, in longitudinal cross-section, of structure provided in the preferred embodiment for adjusting the depth-of-cut during use of the tool to make incisions in soft tissue.

FIG. 3 is an enlarged partial cross-sectional view of a portion of the preferred embodiment, showing a suction junction and details of a switch for powering the surgical tool.

FIG. 4 is a schematic view of a portion of a system for providing suction and certain control functions for use of the preferred embodiment.

FIG. 5 is a schematic diagram to identify inputs and outputs of a control component for use in a system including the preferred embodiment.

DETAILED DESCRIPTION OF THE PREFERRED EMBODIMENTS

Figure 6:
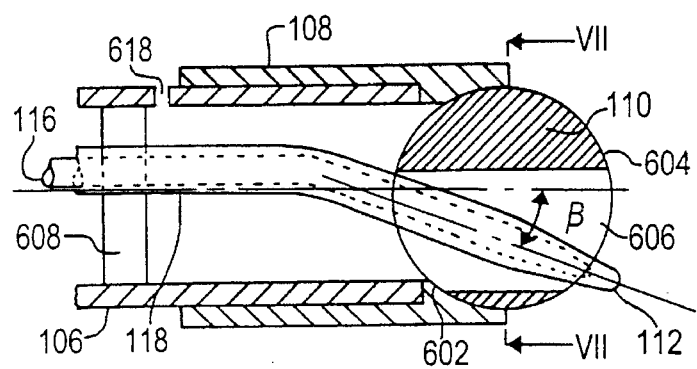
FIG. 6 is a partial longitudinal cross-sectional view of an operative distal end according to one preferred embodiment of this invention.

A preferred embodiment 100 of this invention, as best seen in FIG. 1, has a hand-grip 102 to which is mounted a junction body 104 into which is fitted an elongate cannula-like tubular surgical tool body 106 of suitable length. At a distal end of elongate body 106 is provided an end fitting 108 formed to hold an end element 110 having a smoothly rounded and generally convex surface for contacting soft tissue. Projecting outwardly of the curved surface of end element 110, through a passage formed therein to open to the rounded surface thereof (as described below in greater detail) is a small selected length of a tissue-severing incision tip 112.

Junction body 104 may be provided with one or more controls located to be readily operable by a user grasping hand-grip 102. Such controls may include, for example, an electric switch 114 operable to control a laser energy source and the vacuum source (not shown) which may be connected to an optic fiber 116 extending through junction box 104 and elongate body 106 to carry a controlled flux of laser energy to incision tip 112 as described more fully hereinbelow. Optic fiber 116 is fitted into a protective tubular sheath 118 affixed into an externally-threaded adjustment element 120 which is threaded into a cooperating internally threaded end element 122 at the rear of junction body 104. Into hand-grip 102 are connected a suction line 124 and electrical wiring in a protective insulation sheath 126.

FIG. 2 is a slightly enlarged longitudinal cross-sectional view of threadedly engaged elements 120 and 122. By turning internally threaded element 122 the user can advance or retract, relative to the curved surface of end element 110, the length of optical fiber 116 and, thus, the incision tip 112. This is indicated by the double-headed longitudinal arrows A and A' in FIG. 2. A portion 140 of tubular body 106 extends through junction body 104 and is preferably provided two short internal pins 142, 142 which extend inwardly in a close sliding fit into an external circumferential groove 144 formed in element 122. This ensures a sealed and relatively rotational but axially non-translational relationship between portion 140 and element 122. Consequently, when a user rotates element 122 relative to portion 140, the threaded engagement between elements 120 and 122 non-rotationally moves optic fiber 116 in either the A or A' direction as desired to control the depth of cut as more fully explained below.

FIG. 3 is a partial longitudinal cross-sectional view of junction body 104 and elements inside or immediately adjacent thereto. In addition to the previously discussed elements such as the elongate body 106, junction body 104, and adjustably connected elements 120, 122, FIG. 3 shows a T-junction 128 by which a suction line 130 communicates with an inside annular space defined within elongate body 106 between an outside surface of the protective sheath 118 and an inside surface of the elongate body 106. Through this annular space, as indicated by the plurality of successive arrows in FIG. 3, suction is applied to the distal end of the elongate body 106. Also, within the hand-grip 102 are schematically illustrated two wires 132, 134 which would typically be contained beyond hand-grip 102 in insulation sheath 126. As previously indicated, a user grasping hand-grip 102 may with his or her trigger finger apply sufficient force to switch 114 to activate or deactivate a laser source and a vacuum source connected to wires 132, 134 in known manner. Details of the needed electrical circuitry are considered to be well within the knowledge of persons of ordinary skill in the art.

Suction line 130 is connected to an inlet of a throw-away-type liquid trap 402, wherein any body fluids sucked from the soft tissue being incised by the surgical tool is trapped. An outlet of liquid trap 402 connects to a further portion 404 of the suction line which is provided with a conventional flow transducer 406 to measure a flow rate of gaseous/vaporized materials sucked through elongate body 106. Note that liquid portions of any sucked material are trapped in liquid trap 402 and it is, thus, only the flow rate of gaseous and/or vaporized materials which is measured by flow transducer 406.

Another portion 408 of the suction line connects flow transducer 406 to a pressure transducer 408 of conventional type through a T-junction 410. For performing conventional calibration tests, possibly over a range of operating conditions, the pressure as determined by pressure transducer 408 can be empirically related to the suction flow rate and, by the exercise of control over the applied suction, may be obtained in a range sufficient to bias soft tissue contacted by the curved surface of end element 110 toward the incision tip 112 (as described more fully hereinbelow). The suction line beyond T-junction 410 is connected to a microprocessor-controlled flow control 412 and a solenoid-driven, microprocessor-controlled, flow valve 414. The suction line 416 continues to a suction or vacuum source (not shown).

FIG. 5 is a schematic diagram of a microprocessor 500 to which are provided inputs from flow transducer 406, pressure transducer 408 and switch 114. FIG. 5 also shows exemplary outputs provided to flow control 412 (e.g., an electronic proportional flow valve), a solenoid 414 to turn the vacuum source on and off a laser control 418, and a signal light or audible output device 416. Such a device 416 would inform the user whenever the pressure detected by pressure transducer 406 is within a predetermined pressure range indicative of actual contact of rounded end element 110 to soft tissue such as to block an opening in the rounded surface around incision tip 112.

Experimental data with a prototype system of the kind described above indicates that an optimum range of the actual pressure as determined by pressure transducer 406 is preferably in the range 5–10 psia.

The elongate body 106 is preferably made of seamless stainless steel tubing, and the sheath 118 around optical fiber 116 may be a small-bore, e.g., 2 mm. diameter, stainless steel tube (best seen in FIG. 3). In short, optic fiber 116 is inserted into and is effectively carried by the sheath 118 fitted into externally-threaded element 120 and movable thereby along the length of elongate body 106. By selection of suitably fine threading between elements 120 and 122, very precise and controlled movement is thus made to adjust the depth of cut into the tissue.

Protective sheath 118 is preferably made of thin-walled seamless stainless steel tubing approximately 2 mm. in external diameter. It is swaged to a tissue-penetrating point at its distal end to form the surgical tip 112. The optic fiber 116 is shaped at its distal end to closely fit to the conical inside surface of the swaged end of sheath 118. Optic fiber 116 thus conveys a flux of laser energy which is emitted from its shaped end and is all absorbed by the swaged stainless steel tip 112 which is thereby heated, particularly in the portion projecting outwardly of the rounded surface of end element 110. The essential structure of the conical swaged end of stainless steel sheath and an optic fiber end shaped to fit therein, as described above, is discussed more fully in U.S. Pat. No. 5,306,274 relevant portions whereof are expressly incorporated herein by reference.

Most operating rooms have a so-called "house vacuum system" which can be readily accessed and should be adequate to provide the desired suction. The necessary connections can be of known type. As noted earlier, any known type of pressure transducer and flow rate measurement elements capable of performing over the desired ranges of values may be utilized. Likewise, any known microprocessor may be programmed in conventional manner to ensure that the applied suction and flow rate are controlled within said value ranges.

Attention will now be focused on the structure at the distal end of elongate body 106 to explain exactly how the desired depth of cut is obtained.

Figure 7:
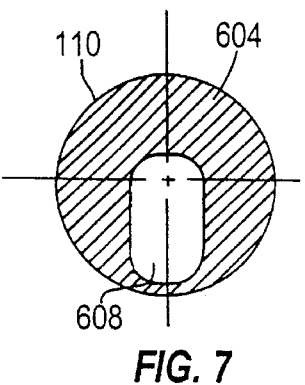
FIG. 7 is a cross-sectional view of a ball-shaped end element provided at the operative distal end at sections VII—VII in FIG. 6.

Referring now to FIG. 6, there is shown in partial enlarged longitudinal cross-sectional view the aforementioned end structure. This includes the distal end of elongate body 106, fitted into end element 108 which has a generally cup-shaped annular surface 602 defining a corresponding circular opening. To this annular surface 602 is preferably fitted a spherical end element 110 which has a smooth rounded external surface 604 and a through passage 606 defining an offset opening 608 (best seen in FIG. 7) in the rounded surface 604.

Figure 8:
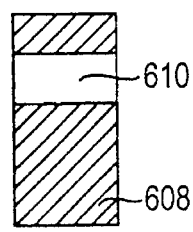
FIGS. 8(A) and 8(B) are respective longitudinal and transverse cross-sectional views of a spacer element for positioning a laser-powered tissue-severing tip portion of an optic fiber according to a preferred embodiment.
Figure 8:
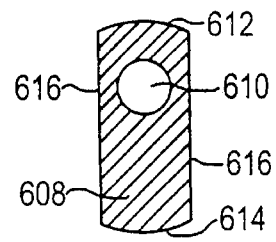

Inside elongate body 106 is provided a support sleeve 608 which is formed with a through aperture 610 sized to closely receive the protective sheath 118, within which optic fiber 116 extends a conically shaped laser energy emitting end fitted into the closed end defining the incision tip 112. As best seen in FIGS. 8(A) and 8(B) sleeve 608 has the through aperture 610 off-center. In the embodiment per FIG. 6 this is needed because the distal end portion of sheath 112 (and the optic fiber inside it) is bent as shown. The combined effect of the off-center aperture 610, offset opening 608, and the bend in sheath 112 is to project tip 112 at an angle "β" relative to the axis of elongate body 106 as best seen in FIG. 6. "β" preferably is in the range 20°–60°.

Note also that support sleeve 608 does not have a complete circular periphery but, instead, in end view per FIG. 8(B) has a shape defined by two arcuate portions 612 and 614 (with 612 being closest to aperture 610), and two straight planar sides 616, 616 symmetrically disposed on opposite sides of aperture 610. With this configuration, even when protective sheath 118 substantially occupies aperture 610 and is supported thereby, flow induced by applied suction can easily convey fluids received through passage 608 in end element 110 past sides 616, 616 of support sleeve 608.

Referring to FIG. 6, very close to the distal end of elongate body 106 and through the wall thereof is provided a small hole 618. This small hole 618 ensures that even if opening 608 is entirely covered by soft tissue, gaseous substances around the outside of the distal end of the surgical tool can be sucked through hole 618 to controllably ease the suction-induced biasing force tending to hold soft tissue to the curved surface 604 of end element 110. It is important to appreciate that while some biasing of the soft tissue to the curved surface 604 is desired, the provision of hole 618 ensures that there is continuous flow through the flow transducer 406. As will be appreciated, if the rounded surface 604 of end element 110 is not pressing on soft tissue to such an extent that opening 608 is blocked by the soft tissue, gaseous materials will flow through the through passage 606 via opening 608 and combine with the flow through hole 618. Because of the larger cross-sectional area available to such flow, there will be a corresponding flow rate determined by flow transducer 406 and a corresponding pressure value determined by pressure transducer 408.

However, when soft tissue blocks opening 608, the flow rate will be solely through hole 618 and a pressure difference corresponding to the magnitude of the difference in pressures immediately outside hole 618 and the pressure immediately inside body 106 will determine the bias force tending to hold the soft tissue to rounded surface 604. Under this circumstance, there will be a smaller through flow of gaseous materials as determined by flow transducer 406, and there will be a correspondingly different pressure determined by pressure transducer 408. A small light may be lit or a selected soft sound provided, under the control of the microprocessor, to inform the user when this occurs.

With the embodiment per FIGS. 6, 7, 8(A) and 8(B), the user handling the surgical tool can contact tissue with tip 112 at the angle "β" relative to the axis of body 106. When the distal operative end of the surgical tool is deployed within an insufflated abdominal cavity, having this small angular inclination facilitates viewing by the laparoscopic camera from a side, i.e., the main elongate body 106 is at an angle and not entirely blocking the view of an incision site where tip 112 is performing an incision.

Figure 9:
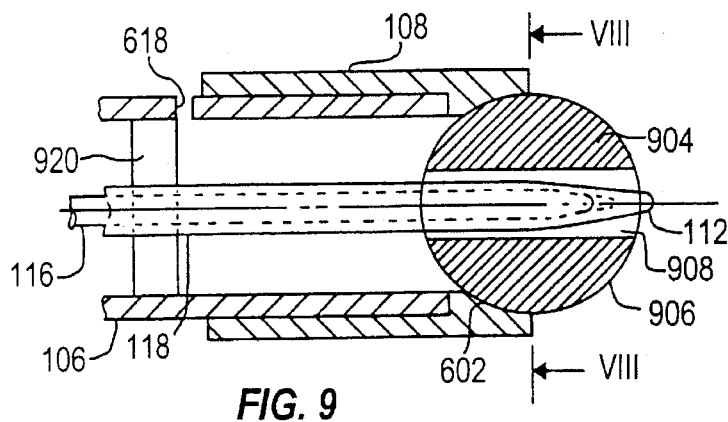
FIG. 9 is a partial longitudinal cross-sectional view of a distal portion of another preferred embodiment of this invention.
Figure 10:
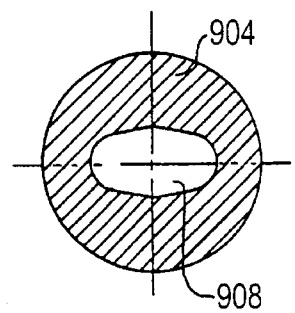
FIG. 10 is a cross-sectional view of a ball-shaped end element at section VIII—VIII according to the preferred embodiment of FIG. 9.

There are, however, other operative circumstances where it may be desirable to have tip 112 aligned with an axis of elongate body 106. Such an alternative embodiment is illustrated in partial enlarged elongate cross-sectional view in FIG. 9. The only significant structural difference between the embodiments per FIGS. 6 and 9 is that the end element 904 has a through passage symmetrical about a diameter and the corresponding opening 908 is centrally symmetrical about the axis of body 106. The exposed rounded surface 910 is thus symmetrically disposed around opening 908.

Figure 11:
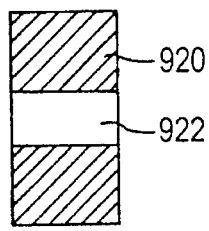
FIGS. 11(A) and 11(B) are respective longitudinal and transverse cross-sectional views of a spacer element for supporting an optic fiber in the preferred embodiment according to FIGS. 9 and 10.
Figure 11:
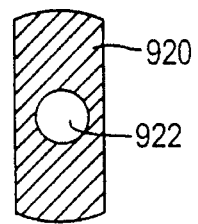

FIGS. 11(A) and 11(B) show how a corresponding support sleeve 920 is provided with a central opening 922 sized to closely receive therein protective sheath 118. In end view, support sleeve 920 has the same outside shape as previously-described support sleeve 608. Accordingly, upon the application of suction to the inside of elongate body 106, any soft tissue contacted by curved surface 906 would be biased toward opening 908, in exactly the same manner as described above with reference to the embodiment per FIG. 6. Similarly, hole 618 is provided to obtain the flow/pressure arrangements exactly as described above with reference to the embodiment per FIG. 6. The main difference in terms of using the embodiments per FIGS. 6 and 9 is that the latter arrangement allows the user to penetrate tip 112 directly forwardly relative to elongate body 106. For certain surgical operations, this may be more advantageous than the angled tip inclined at angle "β" per the embodiment illustrated in FIG. 6. Persons of ordinary skill in the art of performing laparoscopic surgical operations will appreciate such features and may be expected to utilize different embodiments as most appropriate.

Figure 12:
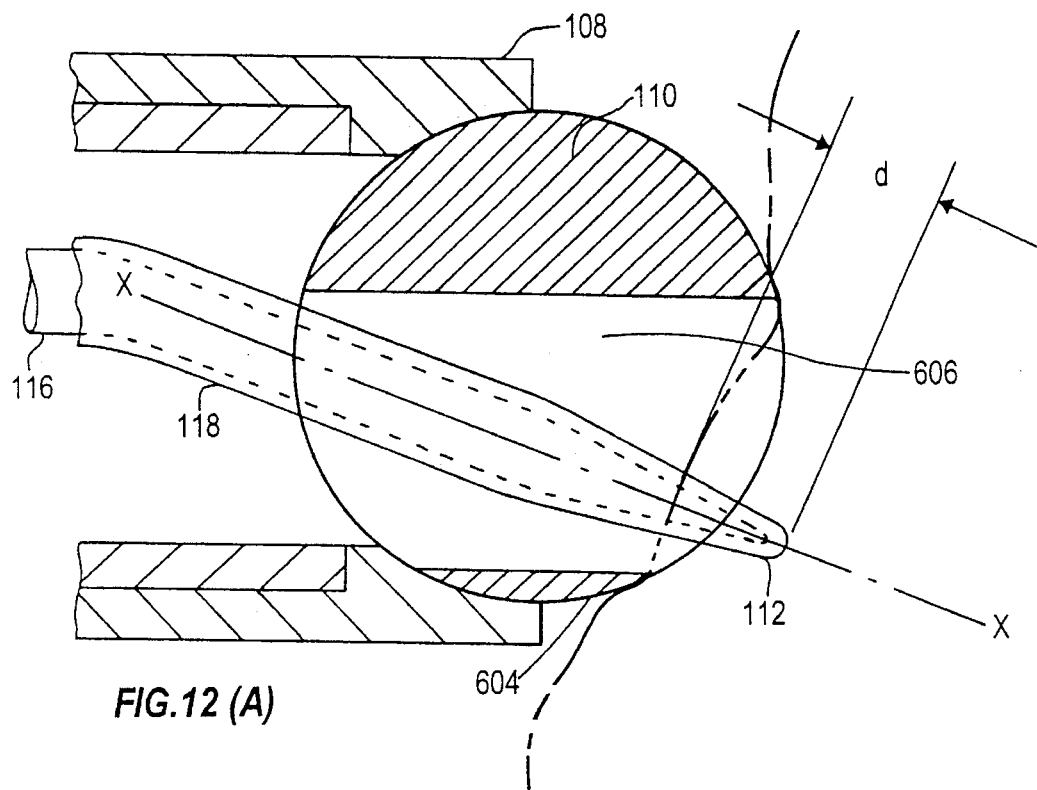
FIGS. 12(A) and 12(B) are respective enlarged longitudinal cross-sectional views to clarify details of how incisions of predetermined depth are ensured.
Figure 12:
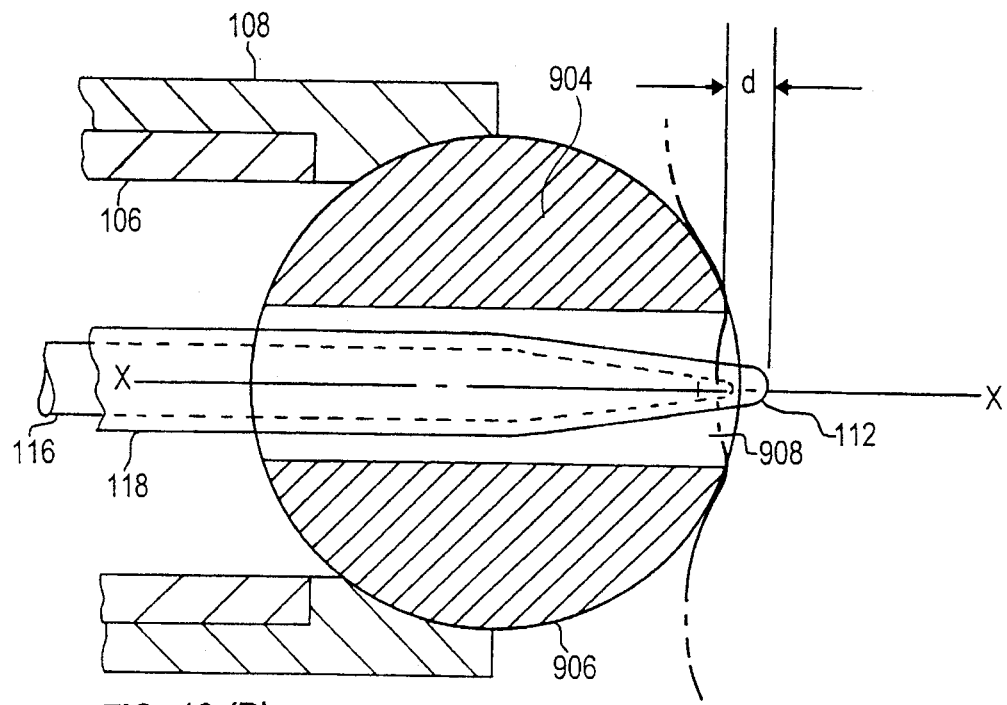
Figure 13:
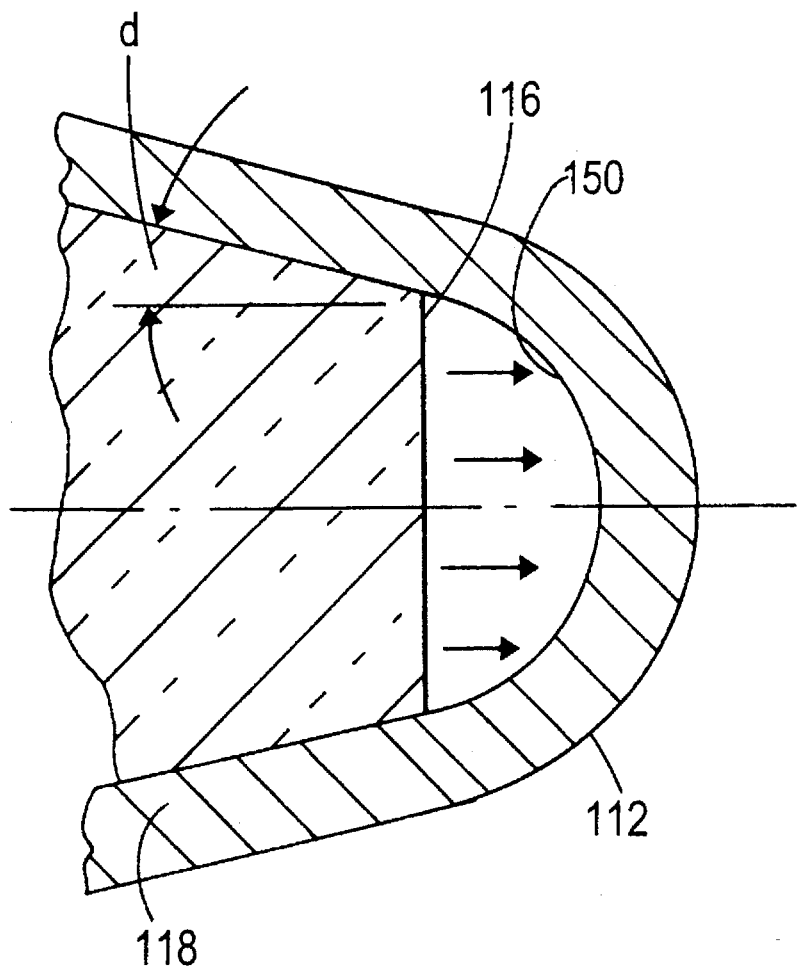
FIG. 13 is a copy of FIG. 6 of U.S. Pat. No. 5,306,274 (incorporated herein by reference), and shows in axial cross-sectional view the distal end portion of a laser-energy transmissive tip element which includes a second material which absorbs laser energy and has a tissue-contacting heated outer surface.
Figure 14A:
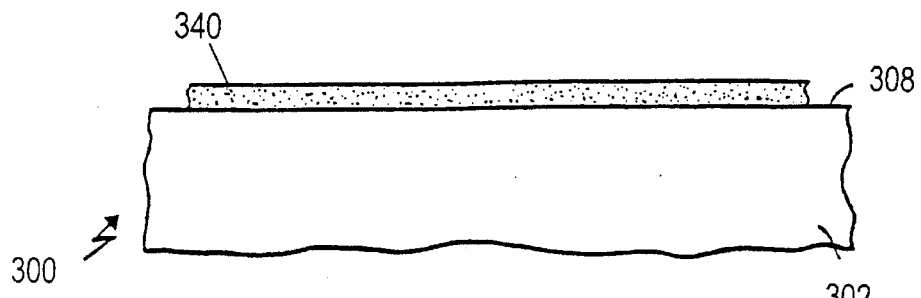
FIGS. 14(A)–14(D) are copies of FIGS. 4A–4D of U.S. Pat. No. 5,164,945, which issued on Nov. 17, 1992 and contains exemplary teaching of a substrate of a first material having a second material securely incorporated into a surface region in a known manner.
Figure 14B:
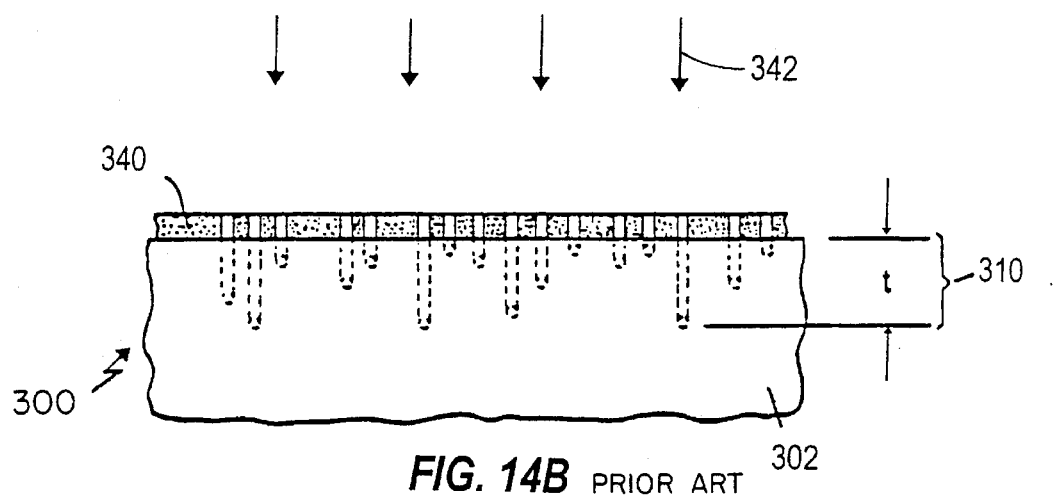
Figure 14C:
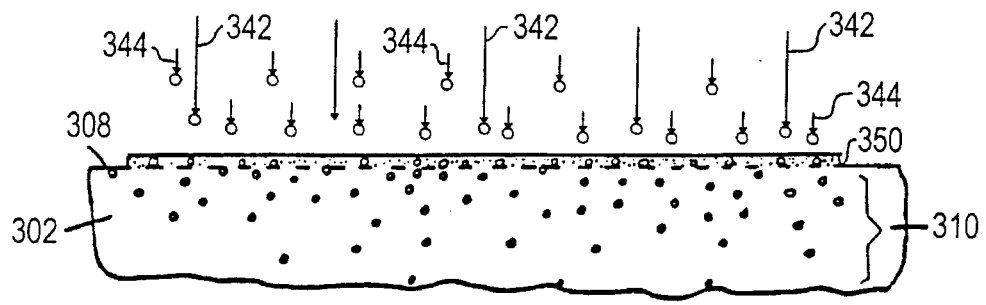
Figure 14D:
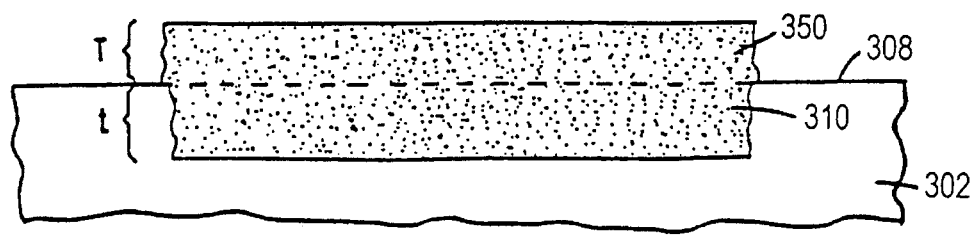

FIGS. 12(A) and 12(B) respectively provide even larger enlarged views of the extreme distal end portions of the surgical tool for the embodiments per FIGS. 6 and 9.

A phantom line is utilized to indicate, in profile, soft tissue to which the respective curved surfaces, i.e., 604 or 906, are contacted while suction is applied.

Because of the softness of the tissue, the contacted surface thereof can be expected to project inwardly of opening 608 very slightly as indicated in FIG. 12(A) and into opening 908 as indicated in FIG. 12(B). The actual penetration of tip 112 into the soft tissue thus disposed, i.e., the effective depth of cut, is identified by the letter "d" and is defined relative to the surface 1000 of the soft tissue where the axis X—X of the tip intersects the same. Persons of ordinary skill in the mechanical arts will immediately appreciate that the precise location of the soft tissue surface within the through passage 606 or 908 (per FIGS. 12(A) and 12(B) respectively) will be a function of the softness and resiliency of the tissue, the suction being applied, the size and shape of the respective openings 608 or 908, and whether or not tip 112 has just penetrated the soft tissue or has been moved after penetration so as to form an incision. The latter circumstance may be expected to tend to very slightly affect the curvature of the soft tissue being further incised immediately adjacent the external surface of tip 112.

It will be appreciated that the depth of cut is thus limited by suitable selection of the shape and size of end element 110 and the openings 608 and 908 provided therein, by appropriate control of the applied suction, and the physical location of tip 112 vis-a-vis the elongate body 106. This, as discussed earlier, can be readily adjusted by user-manipulation of the threadedly engaged elements 120 and 122, as best seen in FIG. 2.

For the type of laparoscopic vagotomy operations discussed above, and for any such operations generally, where it is important that an incision not be made too deep into relatively fragile tissue, e.g., a stomach wall, it is expected that tip 112 would be positioned to generate a depth of cut of the order of 1 mm. to 3 mm. Obviously, with appropriate and obvious variations, depth of cut can be provided to other values. Some skill and professional judgment by the user must of course be involved in adjusting the device to obtain the limited depth of cut.

With a surgical tool according to any of the embodiments described above, because of the inherent strength and stiffness of the thin-walled stainless steel tubing utilized to protect and support the optic fiber 116, and because the swaged end 112 thereof is very hard, the surgeon using the surgical tool according to the present invention can work with the assurance that tip 112 is unlikely to bend or break in normal use. Furthermore, by suitable programming and/or control exercised over the laser energy flux provided to tip 112, the surgeon can control the amount of thermal energy and thus the surface temperature of tip 112 available for thermally-disrupting soft tissue to perform the desired incisions.

Soft body tissues contain a large proportion of water, the balance being organic substances constituting the cells of the tissue. When a relatively hot fine point such as tip 112 is forcibly contacted to such soft tissue, e.g., the exterior of the stomach wall, nerve tissue or small-bore blood vessels, the contacted tissue will immediately become heated and the contacted cells of the tissue will lose sufficient water content to be physically disrupted. Such local breakdown in the cell walls of the tissue will release the cell contents in the immediately vicinity of the hot surface of tip 112. The force applied by the user to the tissue may in the course of forming an incision also close blood vessels and allow the tip to seal them, thereby improving the ability of the tip to coagulate blood and reduce its leakage at the incision site. The water contained in the body fluids, e.g., blood, serum, etc., can be expected to vaporize, some of the organic substances will decompose physically and chemically into gaseous and vaporized byproducts and, as the tip 112 is moved to continue the incision, in effect there will be an open trench left in the wake of the moving tip 112. This trench, i.e., the deliberately formed incision, will have only a limited depth and, because of the high temperature of the tip outer surface at least some of the liquids released from the tissue will be heated to a point where they coagulate locally. However, at least some of the liquids that have not coagulated, and the gaseous/vaporized byproducts, will be sucked by the applied suction immediately past the heated tip 112.

It should be remembered, as taught in detail in U.S. Pat. No. 5,306,274 (incorporated herein by reference) and as generally indicated in the enlarged views per FIGS. 12(A) and 12(B), that laser energy emitted from the end of optic fiber 116 will be received by the inside surface 150 of the stainless steel protective sheath swaged to form the closed-end of tip 112. Stainless steel has the property of absorbing laser energy and converting it into heat. Thus, although stainless steel is also a good thermal conductor, a controlled flux of laser energy can be employed selectively to heat just the extreme distal end portion of tip 112 to perform the necessary thermal disruption of tissue to produce the desired incisions. As soon as the flux of laser energy is terminated, due to thermal conduction along the stainless steel protective sheath 108, tip 112 will almost instantaneously cool down because it has a very small mass and thermal inertia due to its very small size. The surgeon can, therefore, use such a quickly cooled tip to move aside locally incised tissue without necessarily causing further thermal disruption of the contacted tissue.

In the context of laparoscopic vagotomy this facility should enable the surgeon/user to form small incisions of controlled depth, to then nudge aside incised tissue to optically examine the result, and to make further incisions as appropriate. Such a surgeon/user can, also, by very simple adjustment at cooperating elements 120 and 122, readily increase or decrease the depth of cut for subsequent incisions without having to remove the tool from the abdominal cavity.

As will also be appreciated, to ensure that there is adequate insufflation of the abdominal cavity, a small flow of carbon dioxide must be provided to the abdominal cavity as some of the carbon dioxide is sucked away through hole 618. The microprocessor, which receives data signals from flow transducer 406 and pressure transducer 408, can be easily utilized to control the carbon dioxide supply rate to ensure that an adequate supply of carbon dioxide is maintained during a prolonged operation.

To summarize briefly: with the present invention a smoothly rounded surface is pressed to soft tissue, a tissue-disrupting tip is projected through an opening in the curved surface to penetrate into the contacted soft tissue, an incision is obtained as the tip is moved through the soft tissue, and control suction is applied to remove from the incision site any released fluids (including both non-coagulated liquids and gaseous-vaporized byproducts) to ensure a clear field of view to guide the surgeon/user. Use of laser energy to employ a heated tip to make the incisions also provides the advantage that at least some of the liquids released during incision-making will become coagulated due to the high temperature of the tip. The invention thus facilitates the forming of incisions of predetermined limited depth of cut, reduces unnecessary bleeding and leakage, and immediately removes any smoke, gas, and vapors to maintain a clear field of view with a suitable optical device such as a laparoscopic camera. It is considered that this relatively simple structure, with its clean controlled incision-making and continuous cleaning of the incision site by immediate removal of released materials, should greatly facilitate delicate operations like laparoscopic vagotomy. Competent surgeons will, it is believed, readily conceive of numerous surgical operations that can be performed more easily and safely with this invention as compared to conventional techniques.

The rounded end element 110 may be made of any tissue-compatible material such as a metal, Teflon (TM) or other plastics material, or even a ceramic, and may be held to the corresponding curved annular surface 602 by any conventional means, e.g., by adhesion.

It should also be appreciated that laser energy, employed as described above in detail, is within the best mode of the present invention. Persons of ordinary skill in the art may also employ other techniques for heating the tip 112, e.g., electrical resistance provided therein and supplied with a controlled electrical current, infrared energy transmitted optically, etc.

For some applications it may even suffice to use merely a sharp pointed mechanical blade as the tip, omitting the heating aspect entirely. In such an embodiment there should be no gaseous or vaporized materials and no heat-caused coagulation of released fluids, but applied suction would still be useful for removing released liquids which the sharp tip is moved to produce incisions of controlled depth. Such an embodiment may be particularly useful where heat-induced coagulation would be undesirable, e.g., to perform incisions of limited depth into the cornea of an eye.

In another variation utilizing laser energy to provide a heated surface region at a tip, a monofilament optic fiber 116 of sufficient inherent stiffness and made of a laser energy transmissive material may be used. The absorption of transmitted laser energy in a relatively thin surface region of a tissue-disrupting portion of the tip would be conveniently effected by alloying into a laser-energy-absorbing portion of the tip a high temperature melting point material selected from the group consisting of titanium, chromium, nickel, zirconium, molybdenum, tantalum, tungsten, yttria, zirconia and alumina. U.S. Pat. No. 5,164,945 teaches in detail the structural and functional aspects of such a tip and is hereby expressly incorporated herein by reference for such teaching therein. Likewise, as is well known in the art, a laser energy absorbing coating or layer may be provided over the tip surface to absorb laser energy transmitted via the optic fiber to thereby provide the desired heating of tip 112.

Finally, it should also be appreciated that the various embodiments described herein may also be advantageously employed on other than living tissue, e.g., on leather, plastics, wood, etc., to make incisions in artistic contexts.

In this disclosure, there are shown and described only the preferred embodiments of the invention, but, as aforementioned, it is to be understood that the invention is capable of use in various other combinations and environments and is capable of changes or modifications within the scope of the inventive concept as expressed herein.

What is claims is:

1. An improved tool for making precise surgical incisions of predetermined depth into a soft tissue by application to the soft tissue the improvement comprising:

a tip element having a tissue-severing surface at a distal end thereof, tissue-contacting means for providing a tissue-contacting surface for contacting the soft tissue, said tissue-contacting surface being formed to have an opening which surrounds the tip element, whereby the soft tissue being incised is pressed by the tissue-contacting surface and is thereby locally stretched around the tip element within the opening so that only a predetermined length of the tissue-severing surface is permitted to penetrate the soft tissue.

2. The improved surgical tool according to claim 1, wherein:

the tool has a hollow elongate body with a distal end opening within which the tip element is supported to project the tissue-severing surface; and the tissue-contacting means comprises a smooth rounded element fitted to the distal end opening of the tool to provide the tissue-contacting surface, the rounded element being formed to have a through passage with a cross-sectional area larger than a cross-sectional area of the tip element, the tip element being disposed so that an annular passage communicating with the through passage is defined around the tip element and ends in said opening.

3. The improved surgical tool according to claim 2, further comprising:

suction means for applying a controlled suction to the through passage to remove via the annular passage and the through passage any fluids that are generated during incision of the soft tissue away from the tissue-severing surface of the tip element while simultaneously causing the soft tissue to be biased toward the opening in the tissue-contacting surface and the tip element disposed therein.

4. The improved surgical tool according to claim 3, wherein:

the tissue-severing surface of the tip element has an end portion shaped as a point for mechanically penetrating the soft tissue.

5. The improved surgical tool according to claim 3, further comprising:

means for heating the tissue-severing surface of the tip element so that application of the tissue-severing surface to the soft tissue causes thermally-induced local disruption of the soft tissue to produce an incision.

6. The improved surgical tool according to claim 3, wherein:

the tissue-severing surface of the tip element is inclined relative to an axis of the through passage in the rounded element.

7. The improved surgical tool according to claim 3, wherein:

means for controllably locating the tip element relative to the tissue-contacting surface to adjust the predetermined length of the tissue-severing surface permitted to penetrate the soft tissue.

8. The improved surgical tool according to claim 7, wherein:

the tip element comprises a first material transmissive to laser energy and has a surface region comprising a second material for absorbing laser energy transmitted through the first material and converting the same into thermal energy to heat the tissue-severing surface.

9. The improved surgical tool according to claim 8, wherein:

the hollow elongate tool body is provided with a wall aperture communicating an inside of the hollow body with a space outside the hollow body and with the annular passage around the tip, to thereby enable controlled suction to be applied to the soft tissue being incised even when the soft tissue contacted by the tissue-contacting surface entirely covers the opening of the tissue-contacting surface around the tip element.

10. The improved surgical tool according to claim 3, wherein:

the hollow elongate tool body is provided with a wall aperture communicating an inside of the hollow body with a space outside the hollow body and with the annular passage around the tip, to thereby enable controlled suction to be applied to the soft tissue being incised even when the soft tissue contacted by the tissue-contacting surface entirely covers the opening of the tissue-contacting surface around the tip element.

11. The improved surgical tool according to claim 1, wherein:

the tissue-severing surface of the tip element has an end portion shaped as a point for mechanically penetrating the soft tissue.

12. The improved surgical tool according to claim 1, further comprising:

means for heating the tissue-severing surface of the tip element so that application of the tissue-severing surface to the soft tissue causes thermally-induced local disruption of the soft tissue to produce an incision.

13. The improved surgical tool according to claim 12, wherein:

the tip element comprises a first material transmissive to laser energy and has a surface region comprising a second material for absorbing laser energy transmitted through the first material and converting the same into thermal energy to heat the tissue-severing surface.

14. The improved surgical tool according to claim 13, wherein:

the second material is incorporated into the first material to be permanently alloyed therein to form the surface region.

15. The improved surgical tool according to claim 14, wherein:

the second material is selected from the group of high temperature melting point materials consisting of titanium, chromium, nickel, zirconium, molybdenum, tantalum, tungsten, yttria, zirconia and alumina.

16. The improved surgical tool according to claim 12, wherein:

the tissue-severing surface of the tip element is inclined relative to an axis of the through passage in the rounded element.

17. The improved surgical tool according to claim 12, wherein:

means for controllably locating the tip element relative to the tissue-contacting surface to adjust the predetermined length of the tissue-severing surface permitted to penetrate the soft tissue.

18. The improved surgical tool according to claim 1, further comprising:

means for controllably locating the tip element relative to the tissue-contacting surface to adjust the predetermined length of the tissue-severing surface permitted to penetrate the soft tissue.

19. A method of making surgical incisions of limited depth into a soft tissue, comprising the steps of:

providing at an operative distal end of a surgical tool a tissue-contact surface having an opening;

providing in said opening a tissue-severing tip which projects outwardly relative to the tissue-contact surface by a predetermined length;

applying the surgical tool to the soft tissue so that the tissue-contact surface presses on and stretches the soft tissue across the opening, thereby limiting a penetration of the projecting tissue-severing tip into the stretched soft tissue to only a predetermined penetration depth; and moving the applied surgical tool so that the tissue-severing tip makes an incision of an incision depth no greater than said predetermined penetration depth.

20. The method according to claim 19, comprising the further step of:

applying a suction to said opening to thereby bias the stretched soft tissue to the opening, and sucking via the opening and away from the stretched soft tissue any fluids released from the soft tissue as said incision is made.

21. The method according to claim 20, comprising the further step of:

heating the tissue-severing tip to obtain thermal disruption of tissue contacted thereby, so as to make said incision with at least a portion of any liquid released from the soft tissue at the site of incision being thermally coagulated.

22. The method according to claim 21, comprising the further step of:

providing laser energy to the tissue-severing tip to heat the same.

23. The method according to claim 22, wherein:

the tissue-severing tip comprises a body portion made of a first material which is transmissive to laser energy, and a surface region which contains a second material alloyed into the first material, the second material being provided to absorb laser energy transmitted into the first material and converting the same into thermal energy to heat the tissue-severing tip.

24. The method according to claim 19, comprising the further step of:

heating the tissue-severing tip to obtain thermal disruption of tissue contacted thereby, so as to make said incision with at least a portion of any liquid released from the soft tissue at the site of incision being thermally coagulated.

* * * * *